United States Patent [19]

Jervis

[11] Patent Number: 5,067,957
[45] Date of Patent: Nov. 26, 1991

[54] METHOD OF INSERTING MEDICAL DEVICES INCORPORATING SIM ALLOY ELEMENTS

[75] Inventor: James E. Jervis, Atherton, Calif.

[73] Assignee: Raychem Corporation, Menlo Park, Calif.

[21] Appl. No.: 252,019

[22] Filed: Sep. 27, 1988

Related U.S. Application Data

[63] Continuation of Ser. No. 177,817, Mar. 30, 1988, abandoned, which is a continuation of Ser. No. 47,824, May 8, 1987, abandoned, which is a continuation of Ser. No. 865,703, May 21, 1986, Pat. No. 4,665,906, which is a continuation of Ser. No. 541,852, Oct. 14, 1983, abandoned.

[51] Int. Cl.⁵ ............................................. A61M 25/01
[52] U.S. Cl. .................................. 606/108; 606/67; 606/69; 606/78; 128/833; 623/2
[58] Field of Search ............ 623/2; 606/60, 67, 69–76, 606/78, 108; 128/833

[56] References Cited

U.S. PATENT DOCUMENTS

| | | | |
|---|---|---|---|
| 3,348,548 | 10/1967 | Chardack | 128/418 |
| 3,416,531 | 12/1968 | Edwards | 128/348 |
| 3,419,012 | 12/1968 | Williamson | 125/350 |
| 3,500,820 | 3/1970 | Almen | 128/303 |
| 3,516,412 | 6/1970 | Ackerman | 128/418 |
| 3,539,034 | 11/1970 | Tafeen | 128/221 |
| 3,620,212 | 11/1971 | Fannon, Jr. | 128/130 |
| 3,729,008 | 4/1973 | Berkovits | 128/418 |
| 3,740,839 | 6/1973 | Otte et al. | 29/628 |
| 3,786,806 | 1/1974 | Johnson et al. | 128/92 YN |
| 3,857,391 | 12/1974 | Lerner | 128/127 |
| 3,868,956 | 3/1975 | Alfidi et al. | 128/345 |
| 3,889,666 | 6/1975 | Lerner | 128/127 |
| 3,890,977 | 6/1975 | Wilson | 128/418 |
| 3,939,828 | 2/1976 | Mohr et al. | 128/92 B |
| 3,960,147 | 6/1976 | Murray | 128/92 B |
| 4,033,331 | 7/1977 | Guss et al. | 128/2 M |
| 4,035,007 | 7/1977 | Harrison et al. | 285/381 |
| 4,037,324 | 7/1977 | Andreasen | 433/24 |
| 4,149,911 | 4/1979 | Clabburn | 148/11.5 R |
| 4,170,990 | 10/1979 | Baumgart et al. | 128/92 YN |
| 4,197,593 | 4/1980 | Kaster et al. | 3/1.5 |
| 4,205,293 | 5/1980 | Melton et al. | 337/140 |
| 4,230,123 | 10/1980 | Hawkins, Jr. | 128/658 |
| 4,233,690 | 11/1980 | Akins | 623/2 |

(List continued on next page.)

FOREIGN PATENT DOCUMENTS

| | | | |
|---|---|---|---|
| 1001034 | 12/1976 | Canada | 128/93 |
| 0105669 | 4/1984 | European Pat. Off. . | |
| 0129634 | 1/1985 | European Pat. Off. . | |
| 0132344 | 1/1985 | European Pat. Off. . | |
| 1491628 | 11/1972 | Fed. Rep. of Germany . | |
| 2703529 | 3/1978 | Fed. Rep. of Germany . | |
| 3147722 | 6/1983 | Fed. Rep. of Germany . | |
| 3225151A1 | 1/1984 | Fed. Rep. of Germany . | |
| 3305267 | 8/1984 | Fed. Rep. of Germany | 128/92 YN |
| 2529083 | 12/1983 | France . | |
| 8211061 | 12/1983 | France . | |
| 58-25140 | 2/1983 | Japan . | |
| 58-29443 | 2/1983 | Japan . | |

(List continued on next page.)

OTHER PUBLICATIONS

Baumgart et al., "Memory Alloys—Properties, Phenomenological Theory and Applications", 1976 (Reference #1 from Opposition).

Bennsmann et al., "Study of the Memory Alloy Nickel-Titanium and Observations on Its Application in the Field of Medicine", 1979 (Reference 2 from Opposition).

(List continued on next page.)

*Primary Examiner*—Robert A. Hafer
*Assistant Examiner*—Kevin G. Rooney
*Attorney, Agent, or Firm*—Jeffrey G. Sheldon

[57] ABSTRACT

Medical devices which are currently proposed to use elements made from shape memory alloys may be improved by the use of stress-induced martensite alloy elements instead. The use of stress-induced martensite decreases the temperature sensitivity of the devices, thereby making them easier to install and/or remove.

41 Claims, 1 Drawing Sheet

U.S. PATENT DOCUMENTS

| | | | |
|---|---|---|---|
| 4,307,723 | 12/1981 | Finney | 128/349 R |
| 4,310,354 | 1/1982 | Fountain et al. | 75/211 |
| 4,378,811 | 4/1983 | Levitan | 128/757 |
| 4,401,433 | 8/1983 | Luther | 604/159 |
| 4,411,655 | 10/1983 | Schreck | 604/165 |
| 4,425,908 | 1/1984 | Simon | 128/1 R |
| 4,427,000 | 1/1984 | Ueda | 128/6 |
| 4,452,236 | 6/1984 | Utsugi | 128/4 |
| 4,485,816 | 12/1984 | Krumme | 128/334 R |
| 4,490,112 | 12/1984 | Tanaka et al. | 433/20 |
| 4,494,531 | 1/1985 | Gianturco | 128/1 R |
| 4,505,767 | 3/1985 | Quin | 148/402 |
| 4,509,517 | 4/1985 | Zibelin | 128/319 |
| 4,512,338 | 4/1985 | Balko et al. | 128/1 R |
| 4,543,090 | 9/1985 | McCoy | 604/95 |
| 4,556,050 | 12/1985 | Hodgson et al. | 128/1 R |
| 4,586,335 | 5/1986 | Hosoda et al. | 60/528 |
| 4,601,283 | 7/1986 | Chikama | 128/4 |
| 4,616,656 | 10/1986 | Nicholson et al. | 128/630 |
| 4,665,906 | 5/1987 | Jervis | 128/92 YN |

FOREIGN PATENT DOCUMENTS

| | | | |
|---|---|---|---|
| 58-41546 | 3/1983 | Japan . | |
| 58-44047 | 3/1983 | Japan . | |
| 58-50951 | 3/1983 | Japan . | |
| 58-133225 | 8/1983 | Japan . | |
| 62-20827 | 4/1984 | Japan . | |
| 59-97115 | 6/1984 | Japan . | |
| 60-45356 | 3/1985 | Japan . | |
| 64-76824 | 3/1989 | Japan . | |
| 940759 | 11/1980 | U.S.S.R. | 128/92 YN |
| 850067 | 7/1981 | U.S.S.R. | 128/92 YN |
| 1110447 | 8/1984 | U.S.S.R. | 128/92 YN |
| 1113110 | 9/1984 | U.S.S.R. | 128/92 YN |
| 2106190 | 4/1983 | United Kingdom . | |
| 2114005 | 8/1983 | United Kingdom | 128/92 YN |

OTHER PUBLICATIONS

Bensmann et al., "Osteosynthesis Staples Made of Nickel-Titanium, Manufacture, Preliminary Experiments and Clinical Use Thereof", 1982 (Reference #3 of Opposition).

Baumgart et al., "Mechanical Problems in the Use of the Memory Effect for Osteosynthesis Plates", 1977 (Reference #4 of Opposition).

Otsuka et al., Shape Memory Alloys, *Metals Forum*, vol. 4, No. 3 (1981), pp. 142–152.

Dotter, Charles T., Transluminal Expandable Nitinol Coil Stent Grafting: Preliminary Report, *Radiology*, vol. 147, pp. 259–260.

Craigg et al., *Radiology*, (Apr. 1983), vol. 147, pp. 261–263.

Schetky, L. McDonald, "Shape Memory Alloys", *Scientific America*, Nov. 1979, pp. 74–82.

Buehler et al., "55-Nitinol Unique Wire Alloy With A Memory", *Wire Journal*, Jun. 1963, pp. 41–49.

Portsmann et al., "P Wave Synchronous Pacing Using Anchored Atrial Electrode Implanted Without Thoracotomy", Jul. 1972, *The American Journal of Cardiology*, vol. 30, pp. 74–76.

FIG_1

FIG_2

METHOD OF INSERTING MEDICAL DEVICES INCORPORATING SIM ALLOY ELEMENTS

CROSS-REFERENCE TO RELATED APPLICATIONS

This application is a continuation of application Ser. No. 177,817 filed Mar. 30, 1988, now abandoned; which is a continuation of application Ser. No. 047,824 filed May 8, 1987, now abandoned; which is a continuation of application Ser. No. 865,703 filed May 21, 1986, now U.S. Pat. No. 4,665,906; which is a continuation of application Ser. No. 541,852 filed Oct. 14, 1983, now abandoned.

BACKGROUND OF THE INVENTION

Field of the Invention

This invention relates to medical devices incorporating shape memory alloys, and to improvements therein.

Introduction to the Invention

Materials, both organic and metallic, capable of possessing shape memory are well known. An article made of such materials can be deformed from an original, heat-stable configuration to a second, heat-unstable configuration. The article is said to have shape memory for the reason that, upon the application of heat alone, it can be caused to revert, or to attempt to revert, from its heat-unstable configuration to its original, heat-stable configuration, i.e. it "remembers" its original shape.

Among metallic alloys, the ability to possess shape memory is a result of the fact that the alloy undergoes a reversible transformation from an austenitic state to a martensitic state with a change in temperature. This transformation is sometimes referred to as a thermoelastic martensitic transformation. An article made from such an alloy, for example a hollow sleeve, is easily deformed from its original configuration to a new configuration when cooled below the temperature at which the alloy is transformed from the austenitic state to the martensitic state. The temperature at which this transformation begins is usually referred to as $M_s$ and the temperature at which it finishes $M_f$. When an article thus deformed is warmed to the temperature at which the alloy starts to revert back to austenite, referred to as $A_s$ ($A_f$ being the temperature at which the reversion is complete) the deformed object will begin to return to its original configuration.

Many shape memory alloys (SMAs) are known to display stress-induced martensite (SIM). When an SMA sample exhibiting stress-induced martensite is stressed at a temperature above $M_s$ (so that the austenitic state is initially stable), but below $M_d$ (the maximum temperature at which martensite formation can occur even under stress) it first deforms elastically and then, at a critical stress, begins to transform by the formation of stress-induced martensite. Depending on whether the temperature is above or below $A_s$, the behavior when the deforming stress is released differs. If the temperature is below $A_s$, the stress-induced martensite is stable; but if the temperature is above $A_s$, the martensite is unstable and transforms back to austenite, with the sample returning (or attempting to return) to its original shape. The effect is seen in almost all alloys which exhibit a thermoelastic martensitic transformation, along with the shape memory effect. However, the extent of the temperature range over which SIM is seen and the stress and strain ranges for the effect vary greatly with the alloy.

In copending and commonly assigned U.S. patent application Ser. No. 06/541,844 to Quin now U.S. Pat. No. 4,505,767, the disclosure of which is incorporated herein by reference, a nickel/titanium/vanadium alloy having SIM over a wide temperature range is disclosed.

Shape memory alloys have found use in recent years in, for example, pipe couplings (such as are described in U.S. Pat. Nos. 4,035,007 and 4,198,081 to Harrison and Jervis), electrical connectors (such as are described in U.S. Pat. No. 3,740,839 to Otte and Fischer), switches (such as are described in U.S. Pat. No. 4,205,293), actuators, etc.

Various proposals have also been made to employ shape memory alloys in the medical field. For example, U.S. Pat. No. 3,620,212 to Fannon et al. proposes the use of an SMA intrauterine contraceptive device, U.S. Pat. No. 3,786,806 to Johnson et al. proposes the use of an SMA bone plate, U.S. Pat. No. 3,890,977 to Wilson proposes the use of an SMA element to bend a catheter or cannula, etc.

These medical SMA devices rely on the property of shape memory to achieve their desired effects. That is to say, they rely on the fact that when an SMA element is cooled to its martensitic state and is subsequently deformed, it will retain its new shape; but when it is warmed to its austenitic state, the original shape will be recovered.

However, the use of the shape memory effect in medical applications is attended with two principal disadvantages. First, it is difficult to control the transformation temperatures of shape memory alloys with accuracy as they are usually extremely composition-sensitive, although various techniques have been proposed (including the blending by powder metallurgy of already-made alloys of differing transformation temperatures: see U.S. Pat. No. 4,310,354 to Fountain et al.). Second, in many shape memory alloys there is a large hysteresis as the alloy is transformed between austenitic and martensitic states, so that reversing of the state of an SMA element may require a temperature excursion of several tens of degrees Celsius. The combination of these factors with the limitation that (a) it is inconvenient to have to engage in any temperature manipulation, and (b) human tissue cannot be heated or cooled beyond certain relatively narrow limits (approximately 0°-60° C. for short periods) without suffering temporary or permanent damage is expected to limit the use that can be made of SMA medical devices. It would thus be desirable to develop a way in which the advantageous property of shape memory alloys, i.e. their ability to return to an original shape after relatively substantial deformation, could be used in medical devices without requiring the delicacy of alloying control and/or the temperature control of placement or removal needed by present shape memory alloy devices.

DESCRIPTION OF THE INVENTION

Summary of the Invention

I have discovered that if, in a medical device containing a shape memory alloy element which uses the shape memory property of that alloy, an element which shows the property of stress-induced martensite is used instead, an improved device results.

Accordingly, this invention provides a medical device intended for use within a mammalian body, or in such proximity to a mammalian body that the device is substantially at body temperature, which device comprises a shape memory alloy element, the improvement in which comprises the substitution of an alloy element which displays stress-induced martensite at said body temperature for the shape memory alloy element.

DETAILED DESCRIPTION OF THE PREFERRED EMBODIMENTS

The invention will be discussed first by introducing the concept of stress-induced martensite and the effect achievable by its use, and then by examples showing how SIM alloy elements can be substituted for conventional SMA elements in medical devices to achieve the beneficial effect of the invention.

Figure 1:
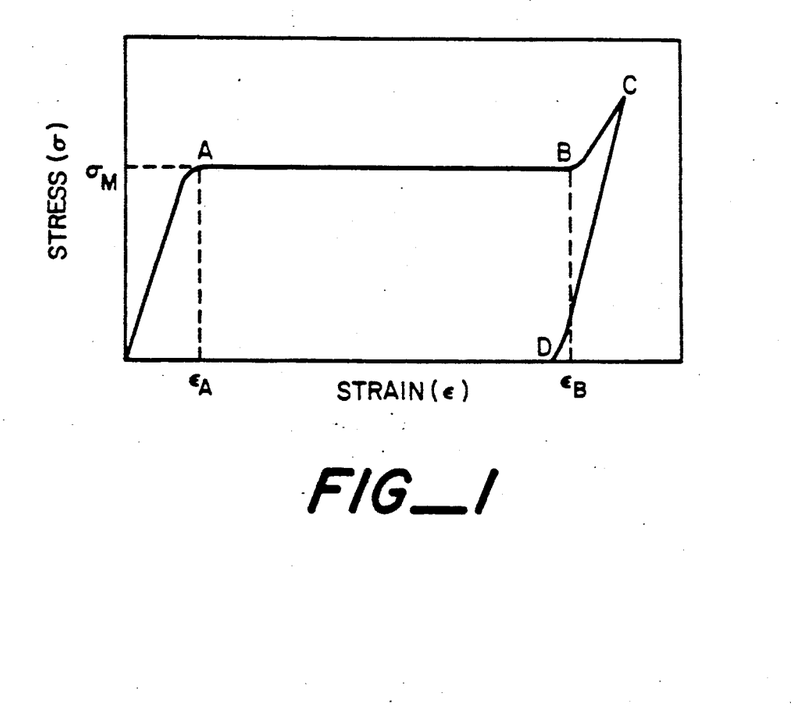
FIGS. 1 and 2 illustrate the stress-strain behavior of an alloy which exhibits constant stress versus strain behavior due to stress-induced martensite.

The Figures illustrate the phenomenon of stress-induced martensite by means of stress-strain curves. In both FIG. 1 and FIG. 2, the alloy is at a temperature between $M_s$ and $M_d$ so that it is initially austenitic; and it will be assumed for the purposes of this discussion that $M_s$ is equal to $M_f$, and $A_s$ equal to $A_f$. FIG. 1 shows the case when the temperature is below $A_s$, so that any martensite formed by the applied stress is stable; while FIG. 2 shows the case where the temperature is above $A_s$, so that austenite is the only stable phase at zero stress.

In FIG. 1, when a stress is applied to the alloy, it deforms elastically along the line OA. At a critical applied stress, $\sigma_M$, the austenitic alloy begins to transform to (stress-induced) martensite. This transformation takes place at essentially constant stress until the alloy becomes fully martensitic at point B. From that point on, as further stress is applied, the martensite yields first elastically and then plastically (only elastic deformation is shown at point C). When the stress is released, the martensite recovers elastically to point D, at which there is zero residual stress, but a non-zero residual strain. Because the alloy is below $A_s$, the deformation is not recoverable until heating above $A_s$ results in a reversion to austenite. At that point, if the sample is unrestrained, the original shape will be essentially completely recovered: if not, it will be recovered to the extent permitted by the restraint. However, if the material is then allowed to re-cool to the original temperature at which it was deformed (or a temperature where SIM behavior of this type is seen), the stress produced in the sample will be constant regardless of the strain provided that the strain lies within the "plateau" region of the stress-strain curve. That is, for a strain between $\epsilon_B$ and $\epsilon_A$, the strain will be $\sigma_M$. This means that a known, constant force (calculable from $\sigma_M$) can be applied over a wide (up to 5% or more for certain Ni/Ti alloys) strain range. Thus, though this resembles the conventional shape memory effect, because the alloy shows SIM and is below $A_s$ a constant force can be achieved.

Figure 2:
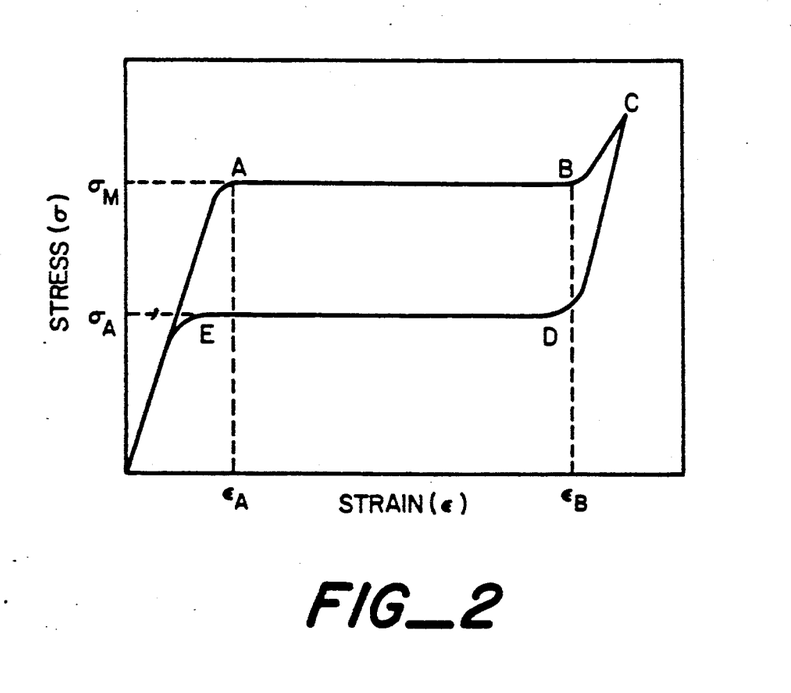

In FIG. 2, when a stress is applied to the alloy, it deforms elastically along line OA, then by SIM along line AB, and by deformation of the martensite to point C, just as in FIG. 1. However, the stress-strain behavior on unloading is significantly different, since the alloy is above $A_s$ and the stable phase is therefore austenite. As the stress is removed, the alloy recovers elastically from C to D; then, at a critical stress, $\sigma_A$, the alloy reverts to austenite without requiring a change in temperature. Thus reversion occurs at essentially constant stress. Finally if the stress is removed from the reverted austenite, it recovers elastically along line EO. The recoverable deformation associated with the formation and reversion of stress-induced martensite has been referred to as pseudoelasticity. While $\sigma_M$ may be comparatively high, e.g. 50 ksi, $\sigma_A$ is usually substantially lower, e.g. less than 10 ksi; thereby creating a constant-force spring with an effective working range of about 5% ($\epsilon_B - \epsilon_A$). The shape change available in the SMA is thus mechanically, rather than thermally, actuated and controlled, permitting a greater control over a device incorporating it.

Suitable alloy for this invention i.e. those displaying stress-induced martensite at temperatures near mammalian body temperature (35°-40° C.), may be selected from known SMAs by those of ordinary skill in the art, having regard to this disclosure by testing for the existence of the SIM effect at the desired temperature. A particularly preferred alloy is the nickel/titanium/vanadium alloy of U.S. patent application Ser. No. 06/541,844 now U.S. Pat. No. 4,505,767, referred to previously.

The following table sets forth transformation temperature data for alloys disclosed in U.S. Pat. No. 4,505,767:

TABLE

| Composition (atomic percent) | | | | |
|---|---|---|---|---|
| Ni | Ti | V | $M_s$ | A(90) |
| 49.50 | 43.50 | 7.00 | −107 | −88 |
| 50.00 | 44.00 | 6.00 | −96 | −84 |
| 49.00 | 43.00 | 8.00 | −83 | −61 |
| 50.00 | 45.00 | 5.00 | −42 | −33 |
| 49.00 | 45.00 | 6.00 | −35 | −12 |
| 50.50 | 48.00 | 1.50 | −32 | −6 |
| 48.50 | 44.50 | 7.00 | −30 | −13 |
| 50.00 | 46.00 | 4.00 | −11 | 7 |
| 48.50 | 45.00 | 6.50 | −10 | 15 |
| 49.00 | 45.50 | 5.50 | −10 | 14 |
| 48.00 | 44.25 | 7.75 | −7 | 8 |
| 48.50 | 45.50 | 6.00 | −5 | 27 |
| 41.50 | 38.50 | 20.00 | −2 | 86 |
| 46.50 | 43.50 | 10.00 | −1 | 50 |
| 36.25 | 33.75 | 30.00 | 0 | 42 |
| 49.50 | 46.00 | 4.50 | 6 | 35 |
| 48.00 | 46.00 | 6.00 | 12 | 36 |
| 47.75 | 45.75 | 6.50 | 20 | 54 |
| 47.50 | 45.50 | 7.00 | 26 | 58 |
| 48.50 | 46.50 | 5.00 | 27 | 58 |
| 45.00 | 45.00 | 10.00 | 30 | 71 |
| 47.50 | 46.50 | 6.00 | 32 | 71 |
| 46.50 | 46.50 | 7.00 | 34 | 70 |

The invention will now be discussed in detail by some Examples of the use of an SIM alloy.

EXAMPLE I

Heart Valves

Akins, in U.S. Pat. No. 4,233,690, the disclosure of which is incorporated herein by reference, describes the use of a shape memory alloy ring to hold a sewing cuff to the body of an artificial heart valve. The ring is made in the austenstic phase, cooled to the martensitic phase, deformed, placed around the valve body, and heated or allowed to warm to cause reversion to the austenitic phase and recovery of the ring into engagement with the valve body.

However, this technique has not found commercial acceptance. Present medical technique requires that the valve body be capable of being rotated relative to the cuff, thereby enabling the surgeon to set the rotational orientation of the valve after it has been sewn into place. This is desirable because the techniques used make it difficult to visualize or accomplish optimal orientation during initial placement.

In order to accomplish the desired torque control to permit the desired rotation and yet ensure a firm hold of the cuff on the valve body, precise control of the pressure exerted on the valve body by the ring is needed. This is difficult because there are substantial manufacturing tolerances in the valve body which may be made, for example, of pyrolytic graphite or ceramics, etc. Because the austenite stress-strain curve is extremely steep, it is not considered practical to use the simple shape memory technique proposed by Akins. Indeed, Akins does not even address the issue of rotation of the cuff with respect to the valve body.

However, if an SIM alloy is used instead of conventional shape memory, the process may be considerably simplified.

First, if the alloy has a stress-strain curve like that of FIG. 1, the alloy ring may be made just as for Akins. The ring is then expanded from its initial austenitic state by the formation of SIM. When the ring is placed about the valve body, it needs only to be heated above $A_f$ and allowed to cool to its original temperature for the ring to engage the valve body with a constant force, even if the valve body has a deviation from the specified size. The torque may thus be controlled to the desired level despite manufacturing tolerances.

Second, if the alloy has a stress-strain curve like that of FIG. 2, the ring may be expanded, placed over the valve body, and the stress released all at the same temperature. Because the austenitic phase is stable, the stress-induced martensite spontaneously reverts to austenite until recovery is restrained by the ring engaging the valve body. Because the reversion to austenite takes place at constant stress, a constant force (and hence constant torque) may be obtained regardless of manufacturing tolerances. Close temperature control is not required, either; and the fact that the patient in a heart valve replacement operation is conventionally cooled as much as 15° C. or so below normal body temperature does not affect the operation of the ring.

To control the torque at a sufficiently low level, it may be desirable for the alloy ring to be other than a solid ring, such as, for example, a continuous helical spring, a flat zigzag spring, etc. Such variations permit the achievement of a greater range of movement with constant force and a reduction in the force exerted by the ring on the valve body, since the ring recovers in a bending mode rather than in tension.

EXAMPLE II

Catheters and Cannulas

Wilson, in U.S. Pat. No. 3,890,977, the disclosure of which is incorporated herein by reference, discloses a catheter or cannula (both being included hereinafter in the word "catheter") made of, or containing, an SMA element to cause all or a portion of the catheter to deploy in a useful form once introduced into a living body.

However, again this device has not been commercialized. Possible defects of the device which have prevented commercialization include (i) the inability to slowly emplace the catheter in a desired position when the transition temperature of the alloy is below body temperature (since the SMA element will attempt to revert to its original shape as it reaches body temperature), thus limiting the ability of the physician to place the device carefully and precisely; or alternatively, if the transition temperature of the alloy is above body temperature, the requirement that the device be heated to a temperature above body temperature to cause recovery and that the device be placed so as not to change shape again when it re-cools (since the body temperature is below the transition temperature); (ii) the inability to remove the device easily; and (iii) the need for controlled temperature storage to prevent premature reversion to austenite of the SMA, with consequent shape change.

The issue of removal of a catheter is especially significant, and not addressed by Wilson. Consider, for example, a tracheal puncture catheter. This should be straight for easy insertion into the trachea through a puncture into the front of the neck, but should curve after insertion so that the flow of air or oxygen through the catheter passes axially down the trachea rather than impinging on the surface of the trachea and damaging it. If a shape memory catheter is used as contemplated by Wilson, it would presumably become austenitic and bend after insertion (see FIGS. 1a and 1b, and corresponding text, of Wilson). But removal would require either cooling to below the transition temperature (which could easily mean cooling to so low a temperature that the tracheal tissue is damaged), removal in the bent shape (presumably damaging tissue), or forcing the austenitic SMA to straighten to permit direct removal (unlikely to be satisfactory since the austenitic alloys e.g. of Ni/Ti may have yield strengths of 100 ksi or more, and force sufficient to cause plastic deformation would be required).

If an SIM element is used instead, however, removal can be accomplished almost as easily as insertion. If the catheter is made in a bent shape (as in Wilson), it can be straightened by insertion of a straight pin down the catheter axis, the catheter deforming by the formation of stress-induced martensite. Insertion of the catheter into the trachea is accomplished while the catheter is straight, at whatever rate is desired (permitting easy and accurate placement), and the pin is gradually withdrawn to permit the catheter to take up its desired shape as the martensite reverts to austenite. [It is assumed here that the stress-strain curve of the alloy at the temperature of use is of the form of FIG. 2, so spontaneous reversion occurs on removal of the stress induced by the pin]. When removal is desired, it may be achieved simply by the gradual insertion of the pin, straightening the catheter and permitting easy withdrawal. Insertion of the catheter into the body and pin removal may, of course, take place simultaneously if desired, as may pin reinsertion and removal of the catheter from the body.

EXAMPLE III

IUDS

Fannon et al., in U.S. Pat. No. 3,620,212, the disclosure of which is incorporated herein by reference, discloses an intrauterine contraceptive device (an IUD) proposed to be formed of a shape memory alloy. The device is suggested to be deformed in the martensitic phase (the transition temperature being below the temperature of the uterus), and the deformed device insulated with, e.g., wax and inserted. Removal is contemplated only by using two SMA elements in opposition, the higher temperature one being martensitic at body temperature but strong enough so that, if heated, it will overcome the lower temperature element and deform the IUD back to a removable shape. The heating contemplated is electrical. The storage problem discussed in Example II also exists here, so that the device must be stored below its transition temperature.

By the use of an SIM element, however, these disadvantages may be overcome. Again, assume that the alloy is SIM psuedoelastic, i.e. that it has the stress-strain curve of FIG. 2. Then an IUD may be formed into the desired shape in the austenitic state, and deformed by compression into a tubular placement device (the deformation being such that the strain levels lie within the "plateau" of the stress-strain curve). When the placement device is inserted into the uterus, the IUD may be deployed by extrusion of the IUD from the placement device. Deployment is then controlled but immediate, so that the physician may satisfy himself with placement. Removal is the reversal of placement: the placement device is inserted into the uterus, the IUD deformed by withdrawal into the placement device, and the placement device withdrawn. Temperature control is not required.

EXAMPLE IV

Bone Plates

Johnson et al., in U.S. Pat. No. 3,786,806, the disclosure of which is incorporated herein by reference, propose the use of Ni/Ti SMA bone plates in fracture fixation. The plate is deformed in its martensitic state, screwed to the two ends of the bone it is desired to compress together, and warmed (or allowed to warm) to the austenitic state, when the plate contracts, compressing the bone ends together. The Johnson et al. bone plate is of generally oblong configuration, overlaps a bone fracture and is secured by two screws to one portion of the bone and by two other screws to the other portion of the bone.

Because of the high elastic moduli of the austenitic shape memory alloys, it will be difficult to control the amount of force which may be applied by a bone plate of the type proposed by Johnson et al., and precision placement of the bone ends and elongation of the plate will be required.

If, however, an SIM pseudoelastic bone plate is used, it will be easily possible to elongate the plate and fasten it to the bone ends without requiring high precision. Because of the comparatively large (e.g. 5%) strain range at essentially constant stress, the force which will be put on the bone ends to compress them will be readily adjustable (by the size of the plate, for example) and will be insensitive to precise placement of the bone ends and/or elongation of the plate. Also, the recovery of the plate, since it is controlled by mechanical restraint, may be as gradual as desired, achieving excellent force and time control, and permitting the surgeon to make adjustments as desired.

EXAMPLE V

Marrow Nails

Baumgart et al., in U.S. Pat. No. 4,170,990, the disclosure of which is incorporated herein by reference, discloses the use of the two-way shape memory effect (where an SMA element exhibits a first shape in the austenitic state and a second in the martensitic state, and spontaneously changes between the two shapes with a change in temperature) in, inter alia, marrow nails (see FIGS. 1a through 1e, and corresponding text, of Baumgart et al.). Marrow nails according to Baumgart et al. comprise a tube of memory alloy which has been split along its longitudinal axis and which may have a circular, elliptical, clover-leaf or other rotation preventing cross section, which may also be variable along the axis of the nail. A prepared marrow nail having a reduced diameter is loosely inserted into a slightly, or not at all, pre-drilled marrow channel of a bone which has been broken or fractured. By means of a heating probe the marrow nail is heated and thus expands. This achieves a relative fixing of the two bone ends along the marrow channel axis. Compression of the fracture is effected by the available muscle tension. If it should be necessary, the marrow nail may also be additionally prestretched along its longitudinal axis so that it is additionally compressed in the longitudinal direction when heated. In this case it is necessary, however, to anchor the nail at both of its ends which anchoring can be effected, for example, by sprockets or teeth on the outer surface of the nail.

The method proposed, however, requires the use of a wide temperature range in order to cause the phase change which is the origin of the two-way shape memory effect (5° C. to 60° C. for the water used to cool or heat the nail). In addition, it requires the manufacture of two-way shape memory elements, which is generally more complex than the manufacture of conventional shape memory elements; and precise control of the transition temperature is required.

However, if an SIM pseudoelastic alloy element is employed, these disadvantages may be overcome. If internal tangs, which may be gripped by an inserted tool, are provided within a marrow nail of the type shown in FIG. 1a of Baumgart et al., then the nail may be radially compressed by the application of stress by such a tool. When the nail is released by the tool, it will expand to fill the bone channel with a constant force (not readily available by Baumgart et al.); and it may be withdrawn by the reverse procedure.

EXAMPLE VI

Dental Arch Wire

Andreasen, in U.S. Pat. No. 4,037,324, the disclosure of which is incorporated herein by reference, proposes the use of dental arch wires made of Ni/Ti alloys instead of conventional 18-8 stainless steel wires. The wires are stated to be of lower elastic modulus and higher elastic limit than stainless steel, which is stated to be advantageous. Heat recovery of an SMA wire is also suggested as a technique for orthodonture.

The technique of using the conventional shape memory effect is not believed to have found clinical application, possibly because such a technique would require rapid placement of the wire in its martensitic state to avoid premature recovery, and would result in rapid recovery with extremely high forces, which would be painful for the patient.

The use of a wire which displays lower elastic modulus and higher elastic limit than stainless steel has found some application, however. Otsuka et al. in Metals Forum, v. 4, pp. 142-52 (1981) have suggested that this behavior may be the result of elasticity enhanced by cold working and martensite-to-martensite psuedoelasticity in an alloy which has a transition temperature below body temperature. The alloy, then, is martensitic rather than austenitic in its undeformed state.

While the use of an enhanced elasticity wire may offer some advantages over the more usual stainless steel wire, it remains the situation that the amount of motion in the teeth that may be produced by an arch wire without further adjustment is largely limited by the pain tolerance of the patient (since the force applied by the arch wire is proportional to the deformation of the wire). However, if an SIM pseudoelastic wire is used, it can exert a relatively constant force (chosen by the dentist to be sufficient to cause tooth movement but not painful) over a strain range of up to 5%. The load may be applied mechanically, and is thus more readily established, and no precise temperature control of the alloy is needed as would be required for the shape memory effect.

EXAMPLE VII

Coil Stents and Filters

The use of tubular coiled wire stent grafts has been discussed in the medical literature since 1969. Although the coils helped maintain patency of the vessels in which they were placed, they were difficult of insertion unless narrow enough to significantly narrow the lumen of the vessel. Recently it has been proposed, see Radiology, v. 147, pp. 259–60 and pp. 261–3 (1983), the disclosures of which are incorporated herein by referece, to use SMA wire to form these tubular coils. The wire, which has a transformation temperature below body temperature, is introduced through a catheter after being straightened in its martensitic state. When the wire is heated, the coil re-forms.

Because of the difficulty of controlling the transformation temperature accurately, it has proved necessary to cool the straightened wire during insertion and/or to heat the wire to form the coil after insertion. These procedures add to the complexity of the operation.

If an SIM pseudoelastic wire is used to form the coil, which is then isothermally deformed by loading into a catheter, then the need for temperature control is avoided. The wire remains straight when in the catheter, but re-forms the coil spontaneously when it is extruded from the catheter. Accurate placement is thus readily obtainable, since there is no urgency as might be required with a conventional shape memory effect element.

It has similarly been proposed to use SMA wire to form a filter for emplacement by cathether in the vena cava to trap blood clots. The filter is formed in the austenitic state, the wire straightened in the martensitic state and inserted, and the filter re-forms on warming. Just as for the coil stents discussed above, the use of an SIM pseudoelastic wire would greatly simplify manufacture and insertion of such a vena cava filter, permitting accurate placement with no need for urgency or temperature manipulation.

EXAMPLE VIII

Bone Staples, Clips, etc.

Bone staples are frequently used to hold fragments of fractured bone together when the fracture is fixed, and may be used in some cases as a replacement for bone plates in the same situation. Sometimes the staples are inserted into drilled holes, sometimes merely driven into the bone directly.

It would be desirable to have a bone staple which provided a controlled force between the tines which would tend to hold the staple in place. Shape memory alloys have been proposed for this application, but again the problem of accurate placement while operating quickly enough to prevent the shape change associated with the martensite-to-austenite transition and/or the need for temperature control complicate their use.

If an SIM alloy is used, these disadvantages may be readily overcome. If the alloy is below $A_s$, it may be emplaced in the martensitic state. Brief heating will then be required to cause it to become austenitic, but on recooling to body temperature, a constant force can be achieved. If the alloy is above $A_s$, the staple can be held deformed by a moderate force, then released after insertion to also provide an accurately-known force. In either event, removal is easier than if the alloy is purely austenitic, as discussed above for Examples II and V, for example.

Similarly, SIM alloy (especially alloy which is pseudoelastic, above $A_s$ at its utilization temperature) may be used to manufacture vascular clips, etc. The alloy element here acts as a constant force spring over a wide strain range (greater than conventional elastic metals), resulting in ease of use.

From the foregoing, it is clear that, in a situation where narrow temperature differences are available or preferable, as often is the case in medical applications, mechanically constrained shape change is a much more useful solution than heat actuated shape change. It offers a degree of control heat actuation does not, it offers easier alloy composition control, it eases mating part tolerance requirements, and it offers simple mechanical reversal at minimal stress levels, all without heating, cooling or insulation complications.

It will be obvious to those skilled in the art, having regard to this disclosure, that other variations on this invention beyond those specifically exemplified here, and other medical devices making use of stress-induced martensite, may be made. Such variations are, however, to be considered as coming within the scope of this invention as limited solely by the following claims.

I claim:
1. A method of medical treatment of a mammal which comprises the steps of:
   (a) providing a device comprising an element which comprises a shape memory alloy which displays stress induced martensite behavior at body temperature of the mammal, the element being restrained in a deformed configuration, the restraining means stressing the element thereby inducing stress induced martensite in the alloy;
   (b) positioning the device so that the shape memory alloy element is within a mammalian body or in such proximity to a mammalian body that the element and the restraining means are substantially at body temperature; and
   (c) at least partially removing the restraining means from the element thereby transforming the element from the deformed configuration, the transformation occurring with the element and the restraining means being substantially at body temperature.
2. A method as claimed in claim 1, in which transformation of the shape memory alloy element causes one or more parts of the body in contact with the element to be displaced.
3. The method of claim 1 wherein the step of removing the restraining means transforms the element without change in state of the restraining means.

4. The method of claim 1 wherein the shape memory alloy element is a catheter.

5. A method for installing a medical device within or proximate to a mammalian body such that the device is substantially at body temperature, the method comprising the steps of:
(a) providing a medical device comprising a memory alloy element at least partly formed from a pseudoelastic shape-memory alloy, wherein the shape-memory alloy can display reversible stress-induced martensite at about body temperature such that the shape-memory alloy has a stress-induced martensitic state and an austenitic state, the memory alloy element having (i) a deformed shape when the alloy is in its stress-induced martensitic state and (ii) a different unstressed shape;
(b) engaging the memory alloy element with a restraining means at a temperature greater than the As of the alloy for placing the alloy in its stress-induced martensitic state and the memory alloy element in its deformed shape and subsequently positioning the medical device within or proximate to the body at a temperature greater than the As of the alloy while the memory alloy element remains in its deformed shape; and
(c) while maintaining the temperature of the memory alloy element above the As of the alloy, disengaging the restraining means from the memory alloy element so that at least a portion of the alloy transforms from its stress-induced martensitic state so that the memory alloy element spontaneously transforms from its deformed shape toward its unstressed shape, wherein substantially all of the transformation occurs from removing the restraining means and not from any change in temperature of the device or the restraining means.

6. The method of claim 5 wherein the step of engaging comprises directly contacting the memory alloy element with the restraining means, and the step of disengaging comprises separating the restraining means from the memory alloy element.

7. The method of claim 5 wherein the step of disengaging results in at least a portion of the alloy transforming from its stress-induced martensitic state to its austenitic state.

8. The method of claim 7 including the additional step after step (c) of re-engaging the memory alloy element with the restraining means so that the memory alloy element transforms toward its deformed shape by reversion of at least a portion of the alloy from its austenitic state to its stress-induced martensitic state, wherein the step of re-engaging occurs while maintaining the temperature of the device above the As of the alloy.

9. The method of claim 7 wherein when the memory alloy element is in its unstressed shape, the shape-memory alloy is in its austenitic state, and the step of disengaging causes the memory alloy element to transform completely to its unstressed shape.

10. A method for installing a medical device within or proximate to a mammalian body such that the device is substantially at body temperature, the method comprising the steps of:
(a) providing a medical device comprising a memory alloy element at least partly formed from a pseudoelastic shape-memory alloy, wherein the shape-memory alloy can display reversible stress-induced martensite at about body temperature such that the shape-memory alloy has a stress-induced martensitic state and an austenitic state, the memory alloy element having (i) a deformed shape when the alloy is in its stress-induced martensitic state and (ii) a different unstressed shape;
(b) placing the memory alloy element within a hollow restraining member at a temperature greater than the As of the alloy for placing the alloy in its stress-induced martensitic state and the memory alloy element in its deformed shape, and positioning the medical device within or proximate to the body at a temperature greater than the As of the alloy while the memory alloy element remains in its deformed shape; and
(c) while maintaining the temperature of the memory alloy element above the As of the alloy, causing relative movement between the hollow restraining member and the memory alloy element so that at least a portion of the alloy transforms from its stress-induced martensitic state so that the memory alloy element spontaneously transforms from its deformed shape toward its unstressed shape, wherein substantially all of the transformation occurs from the relative movement and not from any change in temperature of the device or the restraining means.

11. The method of claim 10 wherein the hollow member is a tube and the memory alloy element is axially slidable within the tube, and wherein the step of causing relative movement comprises causing relative axial movement between the tube and the memory alloy element so that at least a portion of the memory alloy element extends out of the tube and thereby spontaneously transforms toward its unstressed shape.

12. The method of claim 10 wherein the step of causing relative movement comprises completely separating the hollow member from the memory alloy element, and wherein at least a portion of the alloy transforms from its stress-induced martensitic state to its austenitic state.

13. The invention of claim 10 wherein the transformation of the alloy occurs without any change in the state of the restraining member.

14. A method for installing a medical device within or proximate to a mammalian body such that the device is substantially at body temperature, the method comprising the steps of:
(a) providing a medical device comprising a hollow memory alloy element at least partly formed from a pseudoelastic shape-memory alloy, wherein the shape-memory alloy can display reversible stress-induced martensite at about body temperature such that the shape-memory alloy has a stress-induced martensitic state and an austenitic state, the memory alloy element having (i) a deformed shape when the alloy is in its stress-induced martensitic state and (ii) a different unstressed shape;
(b) placing a restraining means in the hollow memory alloy element at a temperature greater than the As of the alloy for placing the alloy in its stress-induced martensitic state and the memory alloy element in its deformed shape and positioning the medical device within or proximate to the body at a temperature greater than the As of the alloy while the hollow memory alloy element remains in its deformed shape; and
(c) while maintaining the temperature of the memory alloy element above the As of the alloy, causing relative movement between the restraining means and the memory alloy element so that at least a portion of the alloy transforms from its stress-induced martensitic state so that the memory alloy element spontaneously transforms from its deformed shape toward its unstressed shape, wherein substantially all of the transformation occurs from the relative movement and not from any change in temperature of the device or the restraining means.

15. The method of claim 14 wherein the hollow member is a tube and the restraining means is axially slidable within the tube, and wherein the step of causing relative movement comprises causing relative axial movement between the memory alloy element and the restraining means so that at least a portion of the memory alloy element extends beyond the restraining means and thereby spontaneously transforms toward its unstressed shape.

16. A method for inserting a medical device into a mammalian body comprising the steps of:
  (a) providing a medical device comprising (i) a restraining means and (ii) a memory alloy element at least partly formed from a pseudoelastic shape-memory alloy, wherein the alloy can display reversible stress-induced martensite at about human body temperature such that the alloy has a stress-induced martensitic state and an austenitic state, the memory alloy element having (i) a deformed shape when the alloy is in its stress-induced martensitic state and (ii) a different unstressed shape when the alloy is in its austenitic state;
  (b) directly contacting the memory alloy element with the restraining means at a temperature greater than the As of the alloy for placing the alloy in its stress-induced martensitic state and deforming the memory alloy element into its deformed shape; and
  (c) after step (b), while maintaining the temperature of the device above the As of the alloy, inserting the memory alloy element into the human body and at least partly separating the restraining means from the memory alloy element so that at least a portion of the alloy transforms from its stress-induced martensitic state to its austenitic state so that the memory alloy element spontaneously transforms from its deformed shape toward its unstressed shape, wherein substantially all of the transformation occurs from disengaging the restraining means and not from any change in temperature of the device or the restraining means.

17. The method of claim 16 including the additional step after step (c) of re-engaging the memory alloy element with the restraining means so that the memory alloy element transforms toward its deformed shape by reversion of at least a portion of the alloy from its austenitic state to its stress-induced martensitic state, wherein the step of re-engaging occurs while maintaining the temperature of the device above the As of the alloy.

18. A method for inserting a catheter into a mammalian body comprising the steps of:
  (a) providing a catheter at least partly formed from a pseudoelastic shape-memory alloy, wherein the alloy can display reversible stress-induced martensite at about body temperature such that the alloy has a stress-induced martensitic state and an austenitic state, the catheter having (i) an easy insertion shape when the alloy is in its stressed-induced martensitic state and (ii) a different unstressed shape when the alloy is in its austenitic state;
  (b) stressing the catheter with a restraint at a temperature greater than the As of the alloy for placing the alloy in its stress-induced martensitic state and the memory alloy element in its deformed easy insertion shape;
  (c) after step (b), inserting the catheter into the mammalian body at a temperature greater than the As of the alloy; and
  (d) after step (c), at least partly disengaging the restraint from the catheter so that at least a portion of the alloy transforms from its stress-induced martensitic state to its austenitic state so that the catheter spontaneously transforms from its easy insertion shape to its unstressed shape, wherein substantially all of the transformation occurs from disengaging the restraint and not from any change in temperature of the catheter or the restraint.

19. The method of claim 18 including the additional steps after step (d) of (e) stressing the catheter with the restraint at a temperature greater than the As of the alloy for placing the alloy in its stressed-induced martensitic state and the memory alloy element in its easily inserted shape, and (f) removing the easily inserted catheter from the body.

20. The method of claim 18 wherein a catheter is stressed with an internal restraint.

21. The method of claim 18 wherein the catheter is a cannula.

22. The method of claim 18 wherein the step of disengaging comprises removing the restraint from the catheter.

23. The method of claim 18 wherein the restraint is a pin axially slidable within the catheter.

24. The invention of claim 18 wherein the transformation of the alloy occurs without any changes in state of the restraint.

25. A method for inserting a catheter into a mammalian body such that the catheter is substantially at body temperature, the method comprising the steps of:
  (a) providing a medical device comprising a catheter at least partly formed from a pseudoelastic shape-memory alloy, wherein the alloy can display reversible stress-induced martensite at about body temperature such that the catheter has a stress-induced martensitic state and an austenitic state, the catheter being (i) straightened when the alloy is in its stress-induced martensitic state and (ii) curved when the alloy is in its austenitic state;
  (b) sliding a straight pin down the catheter axis at a temperature greater than the As of the alloy for placing the alloy in its stress-induced martensitic state and straightening the catheter; and
  (c) after step (b), while maintaining the temperature of the catheter above As, inserting the catheter into the body and withdrawing the pin from the catheter so that at least a portion of the alloy transforms from its stress-induced martensitic state to its austenitic state so that the catheter spontaneously transforms from being straightened to being curved, wherein substantially all of the transformation occurs from withdrawing the pin from the catheter and not from any change in temperature of the catheter or the pin.

26. The invention of claim 25 wherein the transformation of the alloy occurs without any change in the state of the pin.

27. The method of claim 25 wherein the catheter is a tracheal puncture catheter, and the step of inserting the catheter into the body comprises inserting the catheter into the trachea.

28. The method of claim 25 or 27 comprising the additional steps, after step (c), of (d) inserting the pin into the catheter so that at least a portion of the alloy transforms from its austenitic state to its stress-induced martensitic state so that the catheter spontaneously transforms from being curved to being straight for permitting easy withdrawal of the catheter from the body; and (e) withdrawing the straightened catheter from the body.

29. The method of claim 25 wherein the step of withdrawing the pin comprises removing the pin from the catheter.

30. A method for inserting a medical device into a mammalian body such that the device is substantially at body temperature, the method comprising:
  (a) providing a medical device comprising a memory alloy element at least partly formed from a pseudo-elastic shape-memory alloy, wherein the shape-memory alloy displays reversible stress-induced martensite at about body temperature such that the shape-memory alloy has a stress-induced martensitic state and an austenitic state, the memory alloy element having (i) a straightened shape when the alloy is in its stressed-induced martensitic state and (ii) a different unstressed shape when the alloy is in its austenitic state;
  (b) placing the memory alloy element into a hollow placement device at a temperature greater than the As of the alloy for placing the alloy in its stress-induced martensitic state and the memory alloy element in its straightened shape; and
  (c) while maintaining the temperature of the memory alloy element above the As of the alloy, extruding the memory alloy element from the placement device into the body so that at least a portion of the alloy transforms from its stress-induced martensitic state so that the memory alloy element spontaneously transforms from being straightened to being in its unstressed shape, wherein substantially all of the transformation occurs from disengaging the restraining means and not from any change in temperature of the device or the placement device.

31. The invention of claim 30 wherein the transformation occurs without any change in the state of the placement device.

32. The method of claim 30 wherein the memory alloy element is an intrauterine contraceptive device, and the step of extruding the memory alloy element from the placement device into the body comprises extruding the device into the uterus.

33. The method of claims 30 or 32 including the additional steps, after step (c), of (d) withdrawing the memory alloy element into the placement device for placing the alloy in its stress-induced martensitic state and thus straightening the memory alloy element; and (e) withdrawing the placement device and the straightened memory alloy element from the body.

34. The method of claim 30 wherein the memory alloy element is a stent graft, and the unstressed shape of the stent graft is a tubular coiled shape, and the step of extruding the memory alloy element into the body comprises extruding it into a vessel of the body.

35. The method of claim 30 wherein the memory alloy element is a filter for trapping blood clots, and the step of extruding the memory alloy element into the body comprises extruding the filter into the vena cava.

36. The method of claim 30, 32, 34, or 35 wherein the step of extruding comprises completely removing the memory alloy element from the placement device.

37. The invention of claim 5, 14, or 16 wherein the transformation of the alloy occurs without any change in the state of the restraining means.

38. The invention of claim 1, 5, 10, 14, 16, or 30 wherein the memory alloy element exerts essentially constant stress during its transformation.

39. The invention of claim 18 or 25 wherein the catheter exerts essentially constant stress during its transformation.

40. The method of claim 10 or 14 wherein the step of causing relative movement results in at least a portion of the alloy transforming from its stress-induced martensitic state to its austenitic state.

41. The method of claim 40 wherein the step of causing relative movement comprises disengaging the restraining means from the memory alloy element, the method including the additional step after step (c) of directly contacting the memory alloy element with the restraining means so that the memory alloy element transforms toward its deformed shape by reversion of at least a portion of the alloy from its austenitic state to its stress-induced martensitic state, wherein the step of directly contacting occurs while maintaining the temperature of the device above the As of the alloy.

* * * * *